United States Patent [19]

Oyama et al.

[11] Patent Number: 5,399,754
[45] Date of Patent: Mar. 21, 1995

[54] PROCESS FOR PRODUCING PERFLUOROCARBOXYLIC ACID FLUORIDE

[75] Inventors: Masayuki Oyama, Takasaki; Kazutoshi Munezawa, Nagoya; Hitoshi Kinami, Annaka, all of Japan

[73] Assignee: Shin-Etsu Chemical Co., Ltd., Tokyo, Japan

[21] Appl. No.: 233,802

[22] Filed: Apr. 26, 1994

[30] Foreign Application Priority Data

Apr. 26, 1993 [JP] Japan .................. 5-121972

[51] Int. Cl.$^6$ .................. C07C 59/13; C07C 51/62
[52] U.S. Cl. .................. 562/851
[58] Field of Search .................. 562/851

[56] References Cited

U.S. PATENT DOCUMENTS

| | | | |
|---|---|---|---|
| 3,412,148 | 11/1968 | Arboqast | 562/851 |
| 3,721,696 | 3/1973 | Sianesi et al. | 562/851 |
| 4,894,484 | 1/1990 | Lagow et al. | 562/851 |
| 4,973,748 | 11/1990 | Strutz | 562/851 |
| 4,973,749 | 11/1990 | Siegemund et al. | 562/851 |
| 4,985,594 | 1/1991 | Blickle et al. | 562/851 |
| 4,987,254 | 1/1991 | Schwertfeger et al. | 562/851 |

FOREIGN PATENT DOCUMENTS

| | | |
|---|---|---|
| 725740 | 1/1966 | Canada . |
| 41739 | 12/1981 | European Pat. Off. . |
| 2924385 | 1/1981 | Germany . |
| 48-02527 | 1/1973 | Japan . |
| 56-38231 | 8/1981 | Japan . |
| 7603411 | 10/1976 | Netherlands . |

*Primary Examiner*—Paul J. Killos
*Attorney, Agent, or Firm*—Oblon, Spivak, McClelland, Maier & Neustadt

[57] ABSTRACT

A process of producing a perfluorocarboxylic acid fluoride having the formula (1):

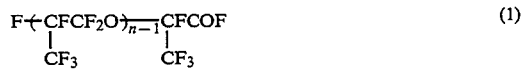

$$F(\underset{CF_3}{CFCF_2O})_{n-1}\underset{CF_3}{CFCOF} \qquad (1)$$

wherein n is an integer of at least 2, comprising effecting oligomerization of hexafluoropropylene oxide in the presence of an alkali metal fluoride a sulfone or a mixture of a sulfone with an ether having the formula (2):

$$CH_3O(CH_2CH_2O)_mCH_3 \qquad (2)$$

where m is an integer of 2 to 6. This process makes it possible to improve production yield of hexafluoropropylene oxide oligomers remarkably, and to raise a reaction temperature for the oligomerization, as compared with conventional methods, thereby shortening reaction time therefor.

6 Claims, No Drawings

PROCESS FOR PRODUCING PERFLUOROCARBOXYLIC ACID FLUORIDE

BACKGROUND OF THE INVENTION

1. Field of the Invention

The present invention relates to a process for producing a perfluorocarboxylic acid fluoride, and particularly to a process for producing a perfluorocarboxylic acid fluoride in a high yield, as compared with conventional processes.

2. Description of the Prior Art

Hitherto, it is known that a perfluorocarboxylic acid fluoride is obtained by oligomerization of hexafluoropropylene oxide (hereinafter referred to as HFPO) in various catalyst/aprotic polar solvent systems. Particularly, as for perfluoro (2-propoxy) propanoic acid fluoride (HFPO dimer), many production processes are disclosed, for example, in Japanese Pre-examination Patent Publication (KOKAI) Nos. 57-45132, 62-175437 and 62-195345. According to these known processes, the HFPO dimer is obtained in a yield of 80% or more.

However, when it is tried to obtain a perfluorocarboxylic acid fluoride with a polymerization degree of three or more (i.e., the HFPO trimer or a further higher oligomer), there occur various problems in which, for example, a mixture of perfluorocarboxylic acid fluorides having a broad molecular weight distribution is produced.

For example, according to Japanese Pre-examination Patent Publication (KOKAI) No. 62-195345, it is possible to obtain the trimer of hexafluoropropylene oxide (an HFPO trimer) by effecting oligomerization of HFPO using cesium fluoride as a catalyst, tetraglyme as an aprotic polar solvent and water as a chain transfer agent. By this method, however, it is necessary to set a reaction temperature as low as 0° to 10° C., and a very long reaction time is required. Furthermore, the resultant product has a broad molecular weight distribution, and the HFPO trimer intended does not exceed 40% in the product obtained. In addition, the product may have a wide batch-to-batch variation in content of the trimer. Further, since perfluoropropanoic acid fluoride, that is, an HFPO isomer is produced in a large quantity, much time is spent in treatment for removing the isomer. These problems cause a large increase in production cost.

SUMMARY OF THE INVENTION

Accordingly, a task of the present invention is to provide a process of producing a perfluorocarboxylic acid fluoride by which it is possible to obtain particularly an HFPO trimer selectively and effectively.

The present invention provides a process of producing a perfluorocarboxylic acid fluoride represented by the following general formula (1):

  (1)

wherein n is an integer of at least 2, comprising effecting oligomerization of hexafluoropropylene oxide in the presence of a catalyst and a solvent, wherein the catalyst is an alkali metal fluoride and the solvent is a sulfone or a mixture of a sulfone with an ether expressed by the following general formula (2):

$$CH_3O(CH_2CH_2O)_mCH_3 \quad (2)$$

where m is an integer of 2 to 6.

DETAILED DESCRIPTION OF PREFERRED EMBODIMENTS

The above-described process is very useful in producing particularly the HFPO trimer which is a perfluorocarboxylic acid fluoride represented by the above general formula (1) wherein n is 3. For example, since in the resultant product the HFPO trimer is contained in an amount of not less than 60%, it is very advantageous as a process to obtain the trimer selectively.

In the present invention, it is very important that oligomerization is effected using as the aprotic polar solvent a sulfone or a mixed solvent of a sulfone with an ether expressed by the general formula (2). Thereby, it has been achieved that the HFPO trimer is particularly obtained in a selectivity of not less than 60% in the product.

The sulfone used as the solvent is a known compound expressed by the following general formula:

wherein R are each a monovalent organic group and the two R may together form a ring containing a sulfur atom. In the present invention any sulfone may be used, and preferably sulfolane (tetramethylene sulfone) is used.

Further, the ether is expressed by the general formula (2) wherein m is preferably 2 to 5, and most preferably the ether is tetraglyme.

The solvent is preferably used in an amount of 0.1 to 30% by weight, particularly 5 to 12% by weight, based on the hexafluoropropylene oxide as the starting material. When a mixed solvent of a sulfone with an ether is used, the sulfone content is preferably not less than 50% by weight, more preferably 80 to 95% by weight, in the mixed solvent.

In the present invention, as the catalyst an alkali metal fluoride is used, which is preferably potassium fluoride. Further, the amount of the catalyst is preferably in a range of 0.01 to 8% by weight, particularly 0.1 to 1% by weight, based on the hexafluoropropylene oxide.

The reaction temperature for oligomerization is preferably in a range of −30° to 110° C. It is important that the use of the aprotic polar solvent as specified above makes it possible to set a higher reaction temperature than conventional processes as well as to improve the selectivity of the HFPO trimer. Therefore, according to the present invention, since the oligomerization can be carried out at a higher reaction temperature, reaction time therefor is remarkably shortened, for example, in half or less of that required in conventional processes. This is a big advantage of the present invention.

In this reaction, an agitation state and reaction temperature have influence on the yield of the HFPO trimer and the degree of polymerization of the HFPO oligomer obtained. Where agitation is vigorous, that is, the catalyst and the solvent are in a high dispersion state, or where reaction temperature is high, the degree of polymerization of HFPO oligomers will be lowered.

On the contrary, where agitation is mild, that is, the catalyst and the solvent are in a low dispersion state, or where reaction temperature is low, the degree of polymerization of HFPO oligomers will be increased.

On the basis of the above-described fact, it is possible to adjust an yield of the HFPO trimer by controlling the agitation state and the reaction temperature.

The oligomerization is readily carried out by supplying hexafluoropropylene oxide in a state wherein the catalyst is dissolved or dispersed in the aprotic polar solvent, and by setting temperature to a prescribed reaction temperature. Preferably, hexafluoropropylene oxide begins to be supplied into the reaction vessel under reduced pressure.

The reaction product thus obtained contains the HFPO trimer in an amount of not less than 60%, and the selectivity of the HFPO trimer is very high. Since no isomer of hexafluoropropylene oxide is produced, it is very easy to separate the catalyst and the solvent from the resultant product. By applying a known refining method such as distillation, it is possible to refine the product without difficulty in a short period of time.

EXAMPLES

Example 1

Into a 300 ml autoclave made of SUS 316 stainless steel and equipped with an agitator, 1.8 g of potassium fluoride and 30 g of sulfolane were charged, and stirred at 40° C. for 30 min. After evacuation of the inside of the autoclave by a vacuum pump, it was initiated to supply hexafluoropropylene oxide (HFPO) therein. Since an exothermic reaction started, by external cooling the autoclave was kept so as to have an internal temperature of 39° C. to 40° C. In addition, the internal pressure of the autoclave was adjusted to 4 kg/cm² by controlling the feed rate of the HFPO.

Thus, 298.6 g of the HFPO was fed over 6 hours. After the HFPO was fed, agitation was further continued until the internal pressure of the autoclave reached about 1 mmHg. Soon after the agitation was stopped, the reaction mixture was separated into two layers, of which the lower layer only was taken out, amounting to 280.4 g. After the reaction product was esterified with methanol, the composition was analyzed by gas chromatography.

The results are given in Table 1. In Table 1, n denotes the degree of polymerization of the resultant HFPO polymers represented by the general formula (1).

TABLE 1

| n | Composition (%) |
|---|---|
| 2 | 26.2 |
| 3 | 63.7 |
| 4 | 9.7 |
| 5 | 0.4 |

Average degree of polymerization: 2.84

Example 2

Into the same autoclave as used in Example 1, 1.8 g of potassium fluoride, 30 g of sulfolane and 6 g of tetraglyme were charged, and stirred at 40° C. for 30 min. After evacuation of the inside of the autoclave by a vacuum pump, it was initiated to supply HFPO therein. Since reaction is accompanied by heat generation, by external cooling the autoclave was kept so as to have an internal temperature between 39° C. and 41° C. In addition, the internal pressure of the autoclave was adjusted to 4 kg/cm² by controlling the feed rate of the HFPO.

Thus, 300.2 g of the HFPO was fed over 3 hours. After the HFPO was fed, agitation was further continued until the internal pressure of the autoclave reached about 1 mmHg. Soon after agitation was stopped, the reaction mixture was separated into two layers, of which the lower layer only was taken out, amounting to 299.4 g.

After esterification of the reaction product with methanol, the composition was analyzed by gas chromatography in the same manner as in Example 1. The results are given in Table 2.

TABLE 2

| n | Composition (%) |
|---|---|
| 2 | 11.2 |
| 3 | 61.8 |
| 4 | 25.4 |
| 5 | 1.7 |

Average degree of polymerization: 3.18

What is claimed is:

1. A process of producing a perfluorocarboxylic acid fluoride represented by the following general formula (1):

$$F\mathord{-}(\underset{CF_3}{CFCF_2O})_{n-1}\underset{CF_3}{CFCOF} \qquad (1)$$

wherein n is an integer of at least 2, comprising effecting oligomerization of hexafluoropropylene oxide in the presence of a catalyst and a solvent, wherein said catalyst is an alkali metal fluoride and said solvent is a sulfone or a mixture of a sulfone with an ether expressed by the following general formula (2):

$$CH_3O(CH_2CH_2O)_mCH_3 \qquad (2)$$

where m is an integer of 2 to 6.

2. The process of claim 1, wherein in said general formula (1) said n is 3.

3. The process of claim 1, wherein said alkali metal fluoride is potassium fluoride.

4. The process of claim 1, wherein said sulfone is sulfolane.

5. The process of claim 1, wherein said catalyst is used in an amount of 0.01 to 8% by weight, based on said hexafluoropropylene oxide.

6. The process of claim 1, wherein said oligomerization is effected at a temperature between −30° C. and 110° C.

* * * * *